US00PP33910P2

(12) United States Plant Patent
Rat

(10) Patent No.: US PP33,910 P2
(45) Date of Patent: Jan. 25, 2022

(54) PEONY PLANT NAMED 'RTPIV 849-04'

(50) Latin Name: ***Paeonia lactiflora* x *Paeonia lutea* hybrid**
Varietal Denomination: RTPIV 849-04

(71) Applicant: Early Morning LLC, Greendale, IN (US)

(72) Inventor: Thierry Rat, Moissac (FR)

(73) Assignee: EARLY MORNING LLC, Greendale, IN (US)

( * ) Notice: Subject to any disclaimer, the term of this patent is extended or adjusted under 35 U.S.C. 154(b) by 0 days.

(21) Appl. No.: 17/340,697

(22) Filed: Jun. 7, 2021

(51) Int. Cl.
*A01H 5/02* (2018.01)
*A01H 6/00* (2018.01)

(52) U.S. Cl.
USPC ..... Plt./316
CPC ..... *A01H 6/00* (2018.05)

(58) Field of Classification Search
USPC ..... Plt./316
CPC ..... A01H 5/02
See application file for complete search history.

*Primary Examiner* — Kent L Bell
(74) *Attorney, Agent, or Firm* — Weatherly IP Solutions, LLC; Barbara Campbell

(57) ABSTRACT

A new and distinct variety of peony plant having double red-purple flowers, a perennial herbaceous shrub, having a compact, symmetrically rounded, and vigorous growth habit, is disclosed.

1 Drawing Sheet

Genus and species: *Paeonia lactiflora* x *Paeonia lutea* hybrid.

Denomination: 'RTPIV 849-04'.

BACKGROUND

'RTPIV 849-04' is a new and distinct variety of *Paeonia lactiflora* x *Paeonia lutea* hybrid. 'RTPIV 849-04' originated from a controlled cross in May 2012 in France between the *Paeonia lactiflora* female parent 'Red Giant' (unpatented) and the *Paeonia lutea* male parent 'Boreas' (unpatented).

The resulting seeds from the cross were collected and planted and evaluated in France. 'RTPIV 849-04' was selected in May 2018 from the population of seedlings in France. 'RTPIV 849-04' was first asexually propagated in September 2020 in France from vegetative cuttings.

'RTPIV 849-04' reproduces true to type in successive generations of asexual reproduction via vegetative cuttings.

SUMMARY

The following are the most outstanding and distinguishing characteristics of this new variety when grown under normal horticultural practices in France.

1. Double red-purple flowers; and
2. A perennial herbaceous shrub, having a compact, symmetrically rounded, and vigorous growth habit.

DESCRIPTION OF THE PHOTOGRAPHS

This new peony plant is illustrated by the accompanying photographs which show the plant's overall plant habit including form, foliage, and flowers. The photographs are of a six to eight years-old plant grown outdoors in France in May 2019. The colors shown are as true as can be reasonably obtained by conventional photographic procedures.

DETAILED DESCRIPTION

Figure 1:
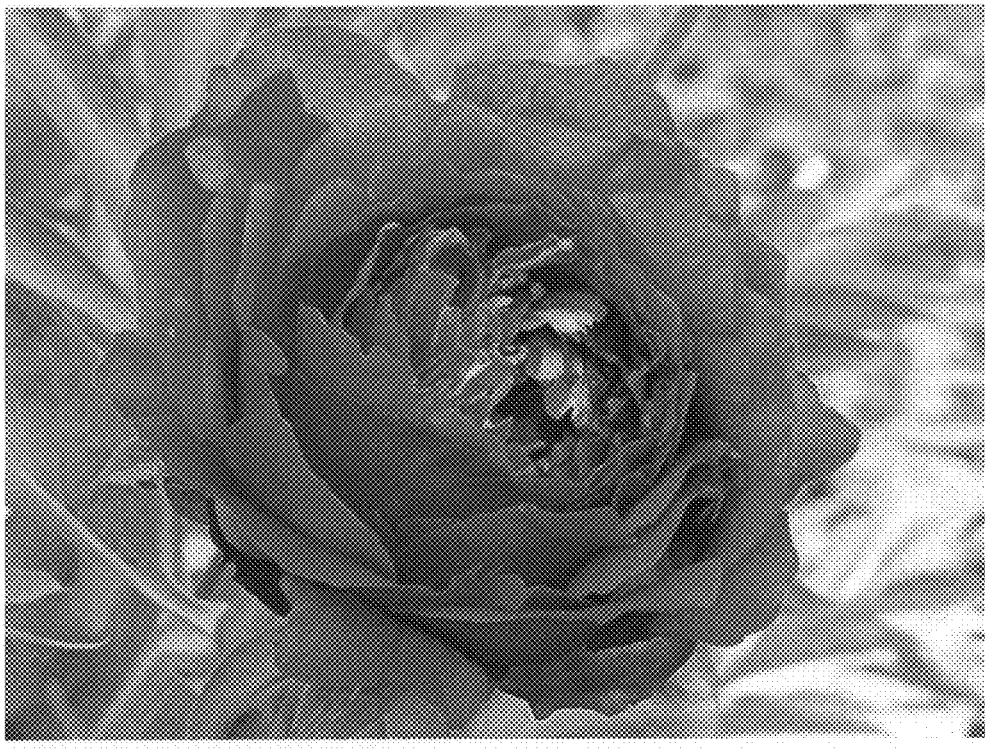
FIG. 1 shows a close-up of a mature open flower, and the foliage of 'RTPIV 849-04'.
Figure 2:
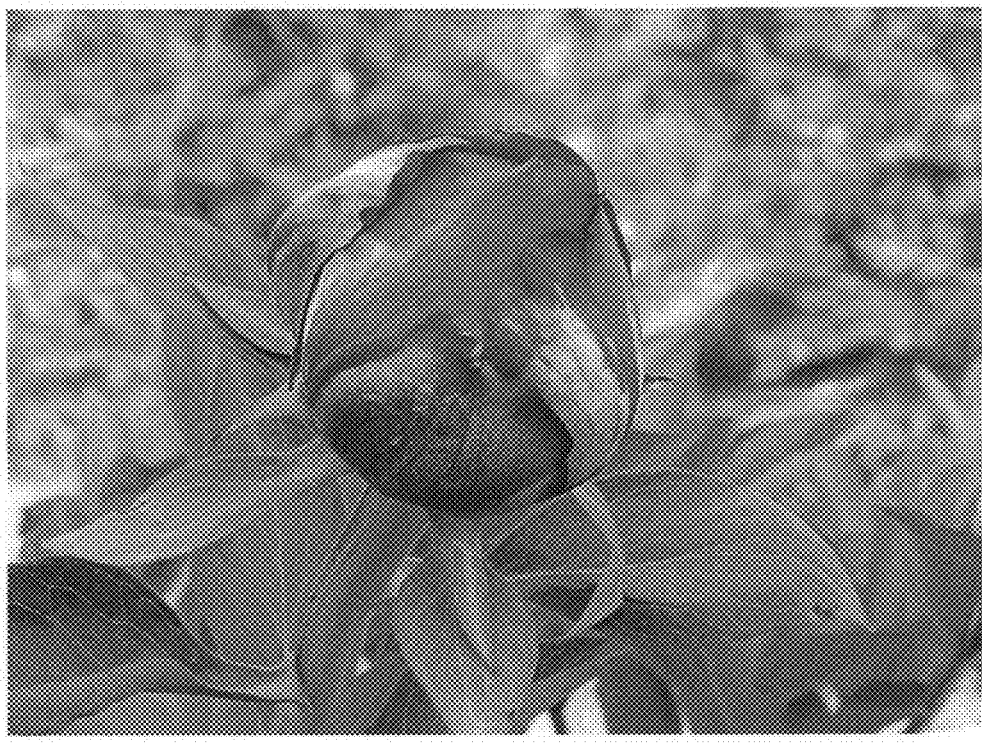
FIG. 2 shows a close-up of an individual bud.

The following detailed descriptions set for the distinctive characteristics of 'RTPIV 849-04'. The data which define these characteristics were collected outdoors in France in May 2018. The plants were six to eight years-old when the descriptions were taken. Color references are to The R.H.S. Colour Chart of The Royal Horticultural Society of London (R.H.S.) 2001, except where general terms of ordinary dictionary significance are used.

Classification:
- *Family*.—Paeoniaceae.
- *Species*.—*Paeonia lactiflora* x *Paeonia lutea* hybrid.
- *Variety*.—'RTPIV 849-04'.

Parentage:
- *Female parent*.—*Paeonia lactiflora* female parent 'Red Giant' (unpatented).
- *Male parent*.—*Paeonia lutea* male parent 'Boreas' (unpatented).

Plant:
- *Type*.—Vegetative cuttings.
- *Root description*.—Fleshy storage root.
- *Rooting habit*.—Freely branching storage and feeder roots.
- *Growth habit*.—Perennial herbaceous shrub; compact and symmetrically rounded; vigorous growth habit.
- *Plant height*.—80.0 cm to 90.0 cm.
- *Plant width*.—100.0 cm to 110.0 cm.

Stem:
- *Quantity of flowers per branch*.—An average of 3.
- *Length*.—80.0 cm to 90.0 cm.
- *Diameter between first and 2nd leaf*.—1.07 cm.
- *Internode length* (*highly variable*).—About 10.0 cm.

*Aspect*.—Mostly upright.
*Strength*.—Strong.
*Color*.—RHS 145A (Yellow-Green).
*Texture*.—Smooth.

Leaf:

*Arrangement*.—Alternate, biternately compound with three primary leaflets further divided into second leaflets of variable number and form.
*Leaf length* (*including petiole*).—40.0 cm.
*Leaf width*.—25.0 cm to 27.0 cm.
*Leaflet length* (*central*).—About 18.0 cm.
*Leaflet width* (*central*).—12.0 cm to 15.0 cm.
*Leaflet shape*.—Broadly elliptical, variably incised.
*Leaflet apex*.—Broadly acuminate, often with emargination.
*Leaflet base*.—Lightly corrugated.
*Leaflet margin*.—Deeply incised.
*Leaflet texture* (*both upper and lower surfaces*).—Smooth, glabrous.
*Leaflet venation pattern*.—Pinnate; reticulate.
*Leaflet color*.—Upper surface: RHS 141B (Yellow-Green). Lower surface: RHS 191B (Yellow-Green).
*Venation color*.—Upper surface: RHS 141B (Yellow-Green). Lower surface: RHS 145B (Yellow-Green).
*Petiole*.—Length (of the 2nd leaf): About 16.0 cm. Diameter: 0.7 cm. Color: RHS 145B (Yellow-Green).

Flower:

*Flower shape, arrangement and flowering habit*.—Double flower/peduncle; flowers are terminal or axillary; flower face is upright to outward; flowers are arranged above the foliage.
*Natural flower season* (*south-west of France*).—Plants begin flowering about 60 days after bud break in early spring.
*Flower longevity*.—Flower last about 10 to 12 days on the plant.
*Fragrance*.—Mild.
*Flower buds*.—Length: 4.0 cm. Diameter: 3.5 cm. Shape: Globose. Color: RHS 184D (Greyed-Purple).
*Flowers*.—Diameter: 17.0 cm to 18.0 cm. Depth: 7.0 cm to 8.0 cm. Petals: Quantity (main flower): About 70 petals with about 90 petaloids. Length: 8.0 cm. Width: 5.0 cm. Shape: Oblong. Apex: Slightly emarginate. Base: Fused. Margin: Entire to slightly sinuate. Texture, upper and lower surfaces: Smooth, glabrous. Color (both upper and lower surfaces): RHS 67C (Red-Purple). Flare (both upper and lower surfaces): RHS 64B (Red-Purple). Petaloids: Length: About 5.0 cm to 6.0 cm. Width: 1.5 cm. Shape and appearance: Narrow, elongated, emarginate on the upper part. Color: RHS 67C (Red-Purple) with RHS 6D (Yellow-Cream) stripes. Sepals: Quantity: 2 small and 3 large. Length: 4.0 cm. Width (outer): 3.5 cm. Shape: Obcordate to obovate; cupped. Apex: Mucronate. Margin: Rounded, slightly emarginate. Color (both upper and lower surfaces): RHS 144C (Yellow-Green) at the base and the upper part is nuanced with RHS 64B (Red-Purple). Texture (both upper and lower surfaces): Smooth. Peduncles (main bud): Length : 18.0 cm to 20.0 cm. Diameter: 0.7 cm. Strength: Strong. Texture: Smooth, glabrous. Color: RHS 145A (Yellow-Green).

Reproductive organs:

*Stamen*.—Quantity per flower: About 80. Filament length: 3.0 cm. Filament color: RHS 6D (Yellow). Anther shape: Elongated and slightly curved. Anther Length : 0.5 cm to 0.6 cm. Anther color: RHS 6A (Yellow). Pollen amount: Moderate. Pollen color: RHS 6C (Yellow).
*Pistil*.—Quantity per flower: Crown of 5 large pistils with 4 smaller pistils in the center. Length: 2.5 cm. Stigma shape: Claw-shaped, convex. Stigma color: RHS 67A (Red-Purple). Ovary color: RHS 142D (Green-Yellow). Ovary appearance: Fluffy.
*Floral disk*.—Strength: Strong. Diameter: 3.0 cm. Color: RHS 145C (Green-Yellow).

Fruit and seed set: Seed production has not been observed.

Disease and insect resistance: Excellent resistance; but no particular susceptibility to diseases or pests.

Temperature tolerance: Hardy like other intersectional hybrid peonies.

COMPARISON WITH PARENTAL AND COMMERCIAL LINES

Table 1 shows a comparison of differences between 'RTPIV 849-04' and both parental lines.

TABLE 1

Comparison with Parental Lines

| Characteristic | 'RTPIV 849-04' | Female parent, 'Red Giant' | Male parent, 'Boreas' |
|---|---|---|---|
| Flower color | Red-Purple | Dark red | Dark burgundy-red |

Table 2 shows a comparison of the differences between 'RTPIV 849-04' and the commercial peony variety 'Coral Charm' (U.S. Plant Pat. No. 4,247).

TABLE 2

Comparison with Commercial Line

| Characteristic | 'RTPIV 849-04' | 'Coral Charm' |
|---|---|---|
| Flower color | Red | Orange-coral |

When 'RTPIV 849-04' is compared to 'RTPIV 849-01' (U.S. Plant patent application Ser. No. 17/340,685), 'RTPIV 849-04' has a plant height of 80 cm to 90 cm, a stem length of 80 cm to 90 cm, and has petaloids, while 'RTPIV 849-01' has a plant height of 60 cm to 70 cm, a stem length of 60 cm to 70 cm and does not have petaloids,

I claim:

1. A new and distinct variety of peony plant designated 'RTPIV 849-04' as illustrated and described herein.

* * * * *